United States Patent
Van Gaalen

(10) Patent No.: US 7,131,443 B2
(45) Date of Patent: Nov. 7, 2006

(54) CONDOM RETAINING DEVICE

(76) Inventor: Garry Joseph Van Gaalen, 11400-89A Ave, Delta (CA) V4C 3G6

( * ) Notice: Subject to any disclaimer, the term of this patent is extended or adjusted under 35 U.S.C. 154(b) by 0 days.

(21) Appl. No.: 10/866,709

(22) Filed: Jun. 15, 2004

(65) Prior Publication Data
US 2005/0274385 A1 Dec. 15, 2005

(51) Int. Cl.
A61F 6/04 (2006.01)

(52) U.S. Cl. .................. 128/844; 128/842; 128/918

(58) Field of Classification Search ............... 128/842, 128/843, 844, 918; 604/327, 328, 346, 347, 604/349, 351, 353
See application file for complete search history.

(56) References Cited

U.S. PATENT DOCUMENTS

| 3,999,550 | A |   | 12/1976 | Martin |   |
|---|---|---|---|---|---|
| 4,354,494 | A |   | 10/1982 | Hogin |   |
| 4,942,885 | A |   | 7/1990 | Davis et al. |   |
| 4,966,594 | A | * | 10/1990 | Thomas | 604/349 |
| 5,076,287 | A |   | 12/1991 | Johnson |   |
| 5,121,755 | A |   | 6/1992 | Hegedusch |   |
| 5,158,556 | A |   | 10/1992 | Starley |   |
| 5,314,447 | A |   | 5/1994 | Papurt |   |
| 5,351,699 | A |   | 10/1994 | Hammons |   |
| 5,360,390 | A |   | 11/1994 | Maanum |   |
| 5,531,230 | A |   | 7/1996 | Bell |   |
| 5,666,971 | A | * | 9/1997 | Anatolievich | 128/842 |
| 5,797,890 | A | * | 8/1998 | Goulter et al. | 604/351 |
| 5,799,657 | A |   | 9/1998 | Pasczuk et al. |   |
| 5,979,448 | A |   | 11/1999 | Weller et al. |   |
| 6,102,043 | A |   | 8/2000 | Johnson |   |
| 6,123,079 | A |   | 9/2000 | Johnson |   |

* cited by examiner

Primary Examiner—Henry Bennett
Assistant Examiner—Camtu Nguyen
(74) Attorney, Agent, or Firm—Oyen Wiggs Green & Mutala LLP

(57) ABSTRACT

A condom retaining device for use with a standard condom has a an elongated elastic strap forming two leg opennngs and a condom-retaining strap forming an opening through which the penis can be inserted. The leg straps encircle the user's legs. The user places a standard condom over the penis down to the base and rolls the open end bead of the condom around an O-ring. The penis is then inserted through the opening in the retainer and the condom with attached ring at the base of the condom is held in place by the retainer.

12 Claims, 3 Drawing Sheets

CONDOM RETAINING DEVICE

TECHNICAL FIELD

The invention relates to the field of prophylactic or contraceptive devices and more particularly to male condoms for preventing disease or conception during sexual intercourse.

BACKGROUND

Condoms have long been used to avoid conception during sexual intercourse and protect against the transmission of sexually-transmitted diseases. The latter function has become even more important since the rise of the HIV AIDS virus. Modern condoms are typically formed of a thin, flexible, elongated cylindrical sheath, sized and shaped to fit the erect male penis, and made of latex or similar liquid-impervious material, closed at one end and open at the other end, and having a bead around the open end around which the condom is rolled for packaging and storage. The effectiveness of the condom is compromised if it slips off the penis of the user during intercourse. Consequently a number of designs have been attempted to ensure that the condom is secured in place during intercourse.

For example, it is known to provide retention straps on condoms which are typically tied around the scrotum of the user. Such designs are shown for example in U.S. Pat. Nos. 4,354,494; 4,942,885; 5,121,755; 5,351,699; 5,531,230; 5,799,657; 6,102,043; 6,123,079 and Canadian patent no. 2,105,341. Such devices require specially constructed condoms and consequently have not received significant acceptance. U.S. Pat. No. 5,158,556 discloses retaining straps which can be clipped to a standard condom but are difficult to install in the heat of the moment. There is therefore a need for a simple condom retaining device which can be used with standard condoms and is easy to put on.

SUMMARY OF INVENTION

The present invention provides a condom retainer which is used in conjunction with a standard condom. It comprises elastic leg straps which encircle the user's legs, and a penis-receiving opening. The user places a standard condom over the penis down to the base and rolls the open end bead of the condom around a ring. The penis is then inserted through the opening in the retaining device and the condom and ring are held in place by the retainer.

BRIEF DESCRIPTION OF DRAWINGS

In drawings which disclose a preferred embodiment of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
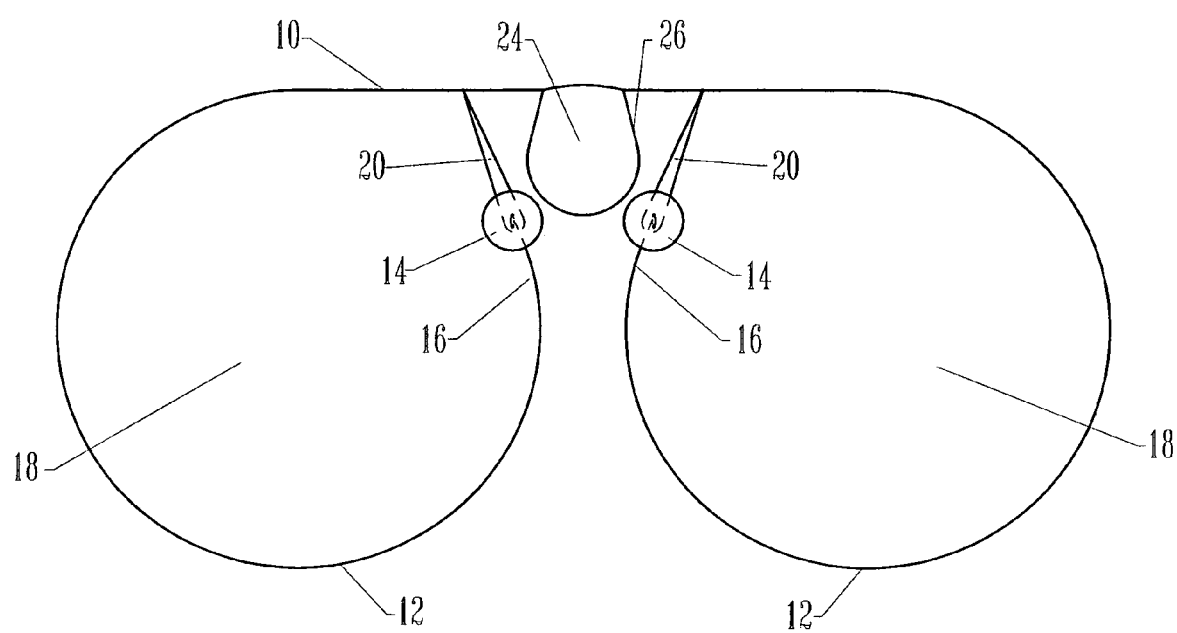
FIG. 1 is a front view of the retaining strap of the present invention.
Figure 2:
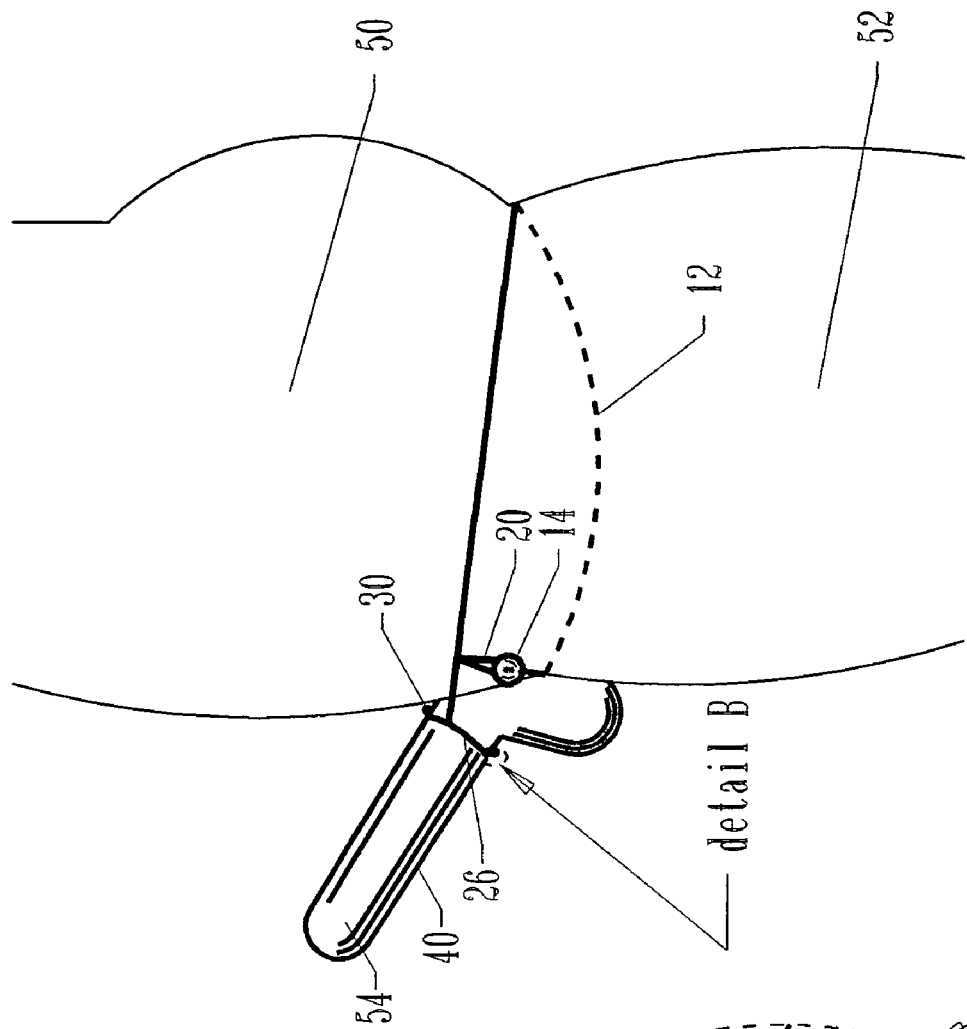
FIG. 2 is a side view of the retaining device of the present invention in place on a user.

With reference to the drawings, the condom retaining device 10 of the present invention comprises a pair of flexible, elastic leg-encircling bands 12 formed of elastic, rubber, polyester braided elastic or similar material which is preferably light and soft in contact with the skin. Alternatively, leg-encircling bands 12 can be formed as a single continuous band 12. Stretchable material with a memory such as polyester or fabric covered elastic about 3 mm in width and 1 mm in thickness is the preferred material. Alternatively bands 12 can be circular or other shape in cross-section, and can be larger or smaller in width or thickness or cross-sectional dimensions. The bands can be knotted, tied, sewn, glued, heat fused or bonded in any other way to form the configuration shown in FIG. 1, or can be molded as a single piece. Preferably the leg openings 18 are formed by providing buttons 14 on ends 16 of leg straps 12, which are hooked into loops 20 attached to bands 12. Other forms of quick-release fasteners such as a hooks or Velcro™ fasteners may be used to form leg openings 18, or the elastic leg-encircling bands 12 may be permanently bonded to form the openings 18. Penis-receiving opening 24 is formed in the device by circular strap 26 attached to leg straps 12. Strap 26 is preferably formed of the same material as straps 12, and is bonded to straps 12 in the same fashion as loops 20, but it may also be formed of different material. The opening 24 thus formed is preferably slightly greater in diameter than the usual diameter of the erect penis, but where elastic material is used may be slightly less than that diameter.

The condom retaining device 10 is used in conjunction with a separate retaining ring 30 and a standard condom 40. Retaining ring 30 is an O-ring formed of rubber, stretchable silicine, latex, polyester or fabric-covered elastic or similar material preferably with a cross-sectional diameter of about 4 mm, or greater. The O-ring has an overall inside diameter slightly greater than the usual diameter of the erect penis.

Figure 3:
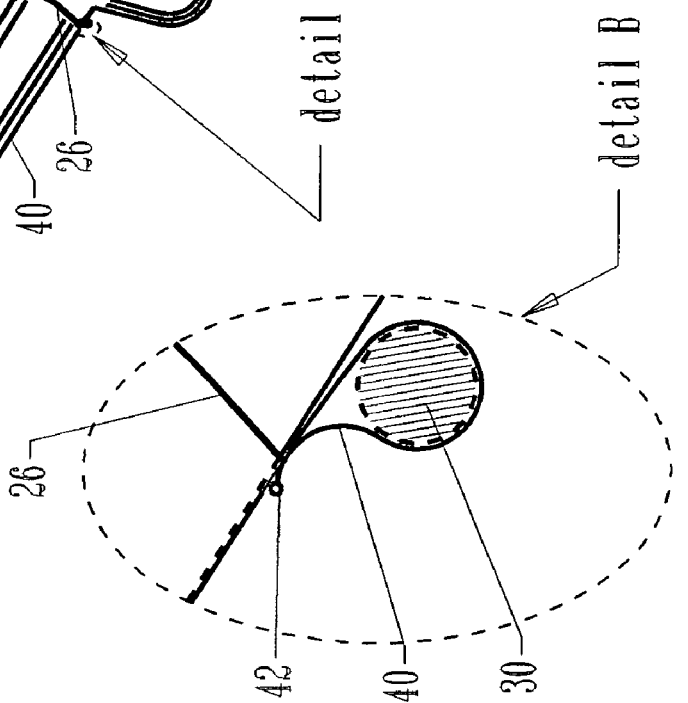
FIG. 3 is a detail of area B of FIG. 2, in partial cross-section.
Figure 5:
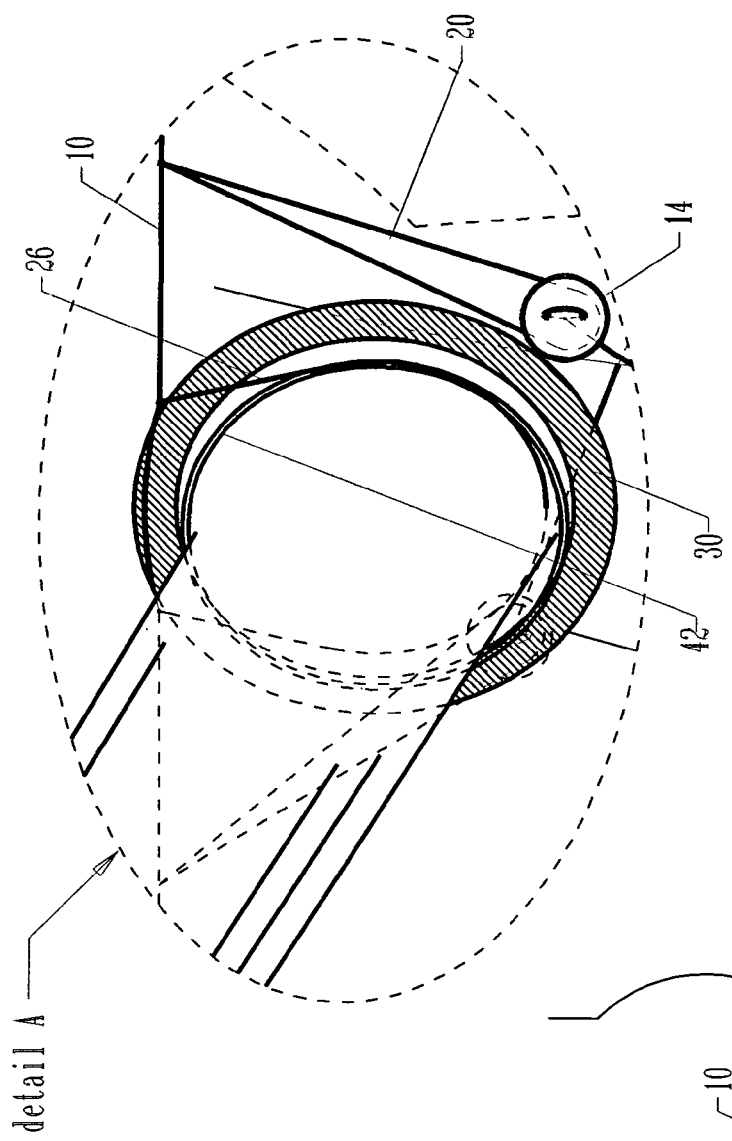
FIG. 5 is a detail of area A of FIG. 4.
Figure 4:
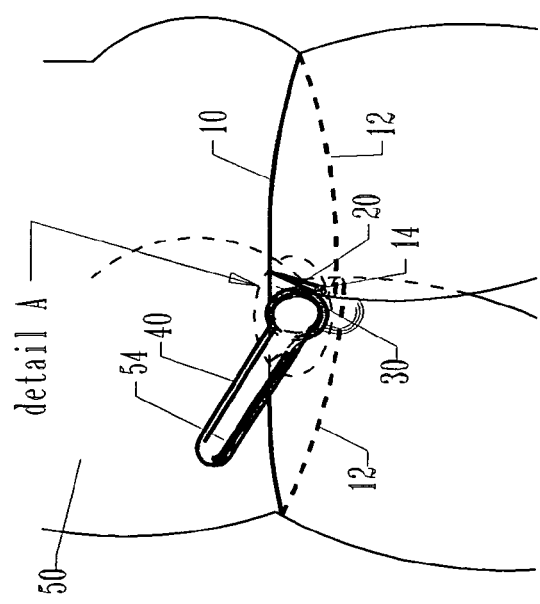
FIG. 4 is a front view of the retaining device of the present invention in place on a user.

To use the device, the user 50 loops the leg straps 12 around each leg 52 and hooks buttons 14 into loops 20. The condom 40 is then placed over the erect penis 54 and rolled down to the base of the penis. Retaining ring 30 is then slipped over the penis 54 to its base and the beaded end 42 of the condom is then rolled over the ring 30 as shown in FIG. 3. Penis 54 with condom 40 and retaining ring 30 installed is then inserted through opening 24 in strap 26. Ring 30 then prevents condom 40 from slipping through strap 26, which in turn is held to the body of the user by leg straps 12.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A condom retaining device for retaining a condom on the penis of a user, said device comprising:

i) a leg-encircling band strap for securing said device to the user's pubic area;

ii) a circular strap having first and second ends, said first and second ends being secured to a leg encircling band strap at two spaced locations centrally thereof proximal to said user's pubic area, thereby forming a loop, said loop forming a penis-receiving opening;

iii) a retaining ring adapted for securing the open end of said condom thereto and having an outside diameter greater than the outside diameter of said penis-receiving opening, said retaining ring being positioned between said loop and said user's pubic area when in use.

2. A method of retaining a condom on a penis during intercourse comprising:

i) providing a device for retaining a condom on the penis of a user, said device comprising a) a leg-encircling band for securing said device to the user's pubic area; and b) a circular strap having first and second ends, said first and second ends being secured to a leg-encircling band strap at two spaced locations centrally thereof proximal to said user's pubic area, thereby forming a loop, said loop forming a penis-receiving opening;

ii) providing a condom having a retaining ring secured around the open end of said condom, said retaining ring having a diameter greater than the diameter of said penis-receiving opening, whereby said retaining ring is positioned between said loop and said user's pubic area when in use, ii) securing said device to The user's pubic area; iii) placing said condom over the penis of the user and securing the open end of the condom around the retaining ring; and iv) inserting the condom-covered penis through said loop.

3. The method of claim 2 wherein said retaining ring is secured around the open end of said condom by folding said open end of said condom around said retaining ring.

4. The condom retaining device of claim 1 wherein said elongated strap forms two leg openings for securing around the legs of the user.

5. The condom retaining device of claim 1 wherein said retaining ring is secured around the open end of said condom by folding said open end of said condom around said retaining ring.

6. The condom retaining device of claim 1 wherein said retaining ring is a flexible ring.

7. The condom retaining device of claim 4 wherein said leg openings are formed by the ends of said elongated strap being releasably fastenable to said elongated strap.

8. The condom retaining device of claim 7 wherein said leg openings are formed by the ends of said elongated strap being releasably fastenable by buttons which are releasably received in loops secured to elongated strap.

9. The condom retaining device of claim 1 wherein said elongated strap is elastic.

10. The condom retaining device of claim 1 wherein said loop is elastic.

11. The condom retaining device of claim 4 wherein said leg openings are formed by the ends of said elongated strap being attached to said elongated strap at intermediate locations thereof.

12. The condom retaining device of claim 7 wherein said leg openings are formed by the ends of said elongated strap being releasably fastenable by hooks which are releasably secured to said elongated strap.

* * * * *